United States Patent [19]
Meijer et al.

[11] 3,980,771
[45] Sept. 14, 1976

[54] PHEROMONE

[75] Inventors: Geertruida M. Meijer, Delft;
Fridolin J. Ritter, Waddinxveen;
Albert K. Minks, Zetten; **Simon
Voerman, Wageningen; Cornelis J.
Persoons**, Pijnacker, all of
Netherlands

[73] Assignee: **Nederlandse Organisatie voor
Toegepast Natuurwetenschappelijk
Onderzoek Ten Behoeve Van
Nijverheid, Handel en Verkeer**, The
Hague, Netherlands

[22] Filed: Jan. 10, 1975

[21] Appl. No.: 540,257

Related U.S. Application Data

[62] Division of Ser. No. 245,199, April 18, 1972, Pat. No. 3,866,349.

[30] Foreign Application Priority Data

Apr. 27, 1971   United Kingdom............... 11634/71

[52] U.S. Cl..................................... 424/84; 424/17
[51] Int. Cl.$^2$.......................................... A01N 17/14
[58] Field of Search................................. 424/84, 17

[56] References Cited
UNITED STATES PATENTS 3,866,349   2/1975   Meijer et al. ...................... 43/114

FOREIGN PATENTS OR APPLICATIONS 7,344,440   6/1973   Japan
7,205,229   10/1972   Netherlands

OTHER PUBLICATIONS

C.A. 76 No. 42109 (1972).
C.A. 75 No. 16792u (1971).
C.A. 73 No. 128348u (1970).
C.A. 69 No. 57094n (1968).
C.A. 70: No. 35485J (1969).
C.A. 74 No. 75981g (1971).
C.A. 76 No. 55545f (1972).
C.A. 77 No. 30289h (1972).
C.A. 78 No. 80915a (1973).
C.A. 80 No. 91981m (1974).
C.A. 79 No. 29576J (1973).
C.A. 79 No. 101717a (1973).

*Primary Examiner*—Shep K. Rose
*Attorney, Agent, or Firm*—Brumbaugh, Graves, Donohue & Raymond

[57] ABSTRACT

A mixture of cis-9-tetradecenyl acetate and cis-11-tetradecenyl acetate can be employed as a powerful attractant for instance in traps to detect or control infestations of the summerfruit Tortrix moth *Adoxophyes Orana* or to confuse the male insect of this species in its search for the female, thereby preventing or diminishing its reproduction.

2 Claims, No Drawings

PHEROMONE

This application is a divisional application of our copending application, Ser. No. 245,199 filed Apr. 18, 1973, now U.S. Pat. No. 3,866,349.

This invention relates to and has among its objects the provision of a mixture of organic compounds and methods of using them for the purpose of attracting male summerfruit tortrix moths to detect and control infestations of this insect species especially in orchards but also in other plantations where this insect needs control. Further objects of the invention will be evident from the following description wherein parts and percentages are by weight unless otherwise specified.

The summerfruit tortrix moth belongs to the species *Adoxophyes orana* (Fischer & von Roslerstamm), also known as *Adoxophyes reticulana* (Hubner) or *Capua reticulana* (Hubner) family Tortricidae, subfamily Tortricinae. It has also been called fruit tree leaf roller.

It constitutes a serious pest in orchards in countries with a moderate climate throughout Europe and Asia. The larvae of the moths attack leaves, shoots and fruit of apple, pear and other fruit trees in particular, but sometimes they also live and feed on other plants.

In order to control or eradicate this pest in a certain area it is necessary to locate the area in which it is present and to determine the degree of infestation in this area. When control has to be carried out by spraying with a toxicant such as an insecticide, this should be done at the time when the freshly hatched egg larvae migrate from the eggs to the parts of the plants on which they feed. This time can be predicted by the determination of time and length of the flight period of the adult moths. (D. J. de Jong, H. Beeke, H. Wondergem, Meded. Dir. Tuinbouw 28 539(1965). This monitoring of the flight period can be effected by setting out, in suspected areas, traps which contain a substance which acts as bait, lure or attractant for the male moths.

The two compounds of the invention constitute such an attractant or pheromone, when mixed in the correct ratio. They are synergists, each of them being ineffective in the absence of the other one.

The pheromone according to this invention consists of a mixture of cis-9-tetradecenyl acetate and cis-11-tetradecenyl acetate. Both substances should be present. As to the ratio of the two compounds the most useful range lies between 0.1 : 10 and 10 : 0.1. It is preferred, however, that the mixture contains more than 50 per cent. of the cis-9 compound and a high biological activity is found if the mixture consists of 1 part of the cis-11 compound and 9 to 3 parts of the cis-9 compound. The optimal value depends on the way of application of the pheromone. The activity is decreased if besides the cis-compounds also the corresponding trans-compound is present in the mixture. An amount of 15 per cent. or more of the trans-compound is decidedly undesirable.

By determining the number of trapped males it is possible to estimate the degree of infestation in a given area. Moreover, traps baited with a mixture of these compounds, when used in conjuncture with a sticky material or with a toxicant, may be applied as a means of control for the summerfruit tortrix.

Another method of control consists in inhibition of mating by "overflooding" an area with the said sex-pheromone(s). According to this method mating can be prevented by saturation of the atmosphere with the attractant. This can be done in various ways, for example by spraying a solution of the said pheromone(s) in an inert solvent or by spraying an aqueous emulsion, or by evaporating into the atmosphere the pheromones, their solution or their emulsion from a number of places in the infested area.

The two active compounds are active in very small quantities. In practice this calls for a diluting agent or carrier in order to obtain a preparation that can be easily handled. A solid carrier such as talcum powder may be used but in daily practice such a solid carrier is not desirable in orchards. Consequently liquid carriers are to be preferred. The type of liquid carrier is not critical. Of course, the authorities must allow the liquid carrier for use in orchards and the like. Also because of the small quantities of the active compounds which are sufficient, the solubility of the active substances in the liquid need not be great. Since there is no need for using such expensive liquid carriers as ethers, esters, alcohol and the like, cheap liquid carriers such as the lower aliphatic liquid hydrocarbons can be advantageously used. Water can also be used but in order to achieve a substantial concentration the active substances may be emulsified in water if necessary with the aid of an emulsifier. It is noted that as yet the synthetic cis-9- and cis-11-tetradecenyl acetate are oils.

Synthesis

Syntheses of cis-9-tetradecenyl acetate have been described by A. A. Sekul & A. N. Sparks, J. Econ. Entomol. 60, 1270 (1967), by D. Wharton, J. Med. Chem. 11, 371 (1968) and H. J. Bestmann, P. Range & R. Kunstmann, Chem. Ber., 104, 65 (1971). The synthesis of cis-11-tetradecenyl acetate has been described by W. L. Roelofs & H. Arn, Nature 219, 513 (1968).

The following examples illustrate the invention.

EXAMPLE I

The sex-pheromone activity of a mixture of cis-9-tetradecenyl acetate and cis-11-tetradecenyl acetate towards male summerfruit tortrix moths was determined in laboratory tests.

Fifteen male moths, about three days old, were placed in cylindrical glass cages of 10 cm diameter and 15 cm height. Both sides of the cages were covered with copper gauze.

A solution of 0.9 micrograms cis-9-tetradecenyl acetate and 0.1 micrograms of cis-11-tetradecenyl acetate in 0.1 ml n-hexane was applied to a piece of filter paper of 4 cm². The solvent evaporated during the dropwise application. The paper was inserted into a Pasteur pipette and by means of a rubber bulb, which was attached to the pipette, an air puff was blown over the paper with the pheromone mixture into the cage with male moths. This elicited the typical behaviour of sexual excitement, such as wing fluttering and copulatory attempts.

The test was carried out at 22°C, with a light intensity of 5 Lux, one hour after closing of the dark period (light regime: 17 hours light, 7 hours dark).

EXAMPLE II

A glass rod of 2 mm diameter and 10 cm length was dipped over a length of 4 cm into a solution containing $4 \times 10^{-8}$ g per ml of a mixture of cis-9-tetradecenyl acetate and cis-11-tetradecenyl acetate (ratio 9 : 1) in hexane.

When the rod was introduced into the cages with male moths, as described in Example I, the moths showed the typical behaviour of sexual excitement.

EXAMPLE III

The effectiveness of mixtures of cis-9-tetradecenyl acetate and cis-11-tetradecenyl acetate as attractants for male summerfruit tortrix moths was determined in field experiments in apple orchards.

The traps which were used in these experiments consisted of two ice cream cups (diameter about 10 cm, height 12 cm), made of carboard lined with wax. The bottoms of the cups were removed and the lower edges of the cups were connected by transparent adhesive tape. In this way traps were formed with two open sides. The lower halves of the cups were lined with a sticky material (treebandlijm, Asepta N.V., Delft, The Netherlands).

A pheromone dispenser containing a mixture of cis-9-tetradecenyl acetate and cis-11-tetradecenyl acetate was placed in the middle of each of the traps. This pheromone dispenser consisted of a hollow polyethylene cap, with removable clipping lid (Kymble products).

Fifteen of such traps, each containing a mixture of 90 micrograms of cis-9-tetradecenyl acetate and 10 micrograms of cis-11-tetradecenyl acetate and another fifteen traps, each containing 75 micrograms of cis-9-tetradecenyl acetate and 25 micrograms of cis-11-tetradecenyl acetate were placed in alternating positions in trees of an apple orchard.

Simultaneously, traps containing no pheromones were set out as a control. The number of moths caught in the traps during the flight period of the summerfruit tortrix are, for each of the series of traps, shown in Table 1.

TABLE 1

| Attractant composition | | number of male summerfruit tortrix moths caught |
|---|---|---|
| cis-9-tetradecenyl acetate, micrograms | cis-11-tetradecenyl acetate, micrograms | |
| 90 | 10 | 475 |
| 75 | 25 | 311 |
| 0 | 0 | 0 |

EXAMPLE IV

A field experiment in an apple orchard was done, similar to that of Example III, but instead of traps, constructed of ice cream beakers, commercially available traps (Sectar insect traps, 3 M Comp. USA) were used. The composition of the pheromone mixture and the captures obtained are shown in Table 2.

TABLE 2

| Attractant composition | | number of male summerfruit tortrix moths caught |
|---|---|---|
| cis-9-tetradecenyl acetate, micrograms | cis-11-tetradecenyl acetate, micrograms | |
| 400 | 0 | 0 |
| 300 | 100 | 135 |
| 200 | 200 | 13 |
| 100 | 300 | 3 |
| 0 | 400 | 0 |
| 0 | 0 | 0 |

EXAMPLE V

A field experiment similar to that of Example IV was done, but both the ratio of the two pheromones and their total amount were varied. The results are shown in Table 3.

TABLE 3

| Attractant composition | | number of male summerfruit tortrix moths caught |
|---|---|---|
| cis-9-tetradecenyl acetate, micrograms | cis-11-tetradecenyl acetate, micrograms | |
| 400 | 0 | 0 |
| 300 | 100 | 148 |
| 200 | 200 | 32 |
| 100 | 300 | 6 |
| 40 | 0 | 0 |
| 30 | 10 | 37 |
| 20 | 20 | 11 |
| 0 | 0 | 0 |

In general the type of sticky substance lining the inner wall of the trap is not critical. Synthetic products may be used as well as e.g. natural waxes.

The traps may consist of transparent materials. This is important. As soon as moths are trapped one can see at once from the outside that the moth is present and this makes it possible by rapid visual inspection to detect the presence of the moths. such a trap may be easily constructed for instance by taking a sheet of celluloid with, say, a width of 15 cm, folding it to a triangular tube and securing the construction with adhesive tape.

As a bottle or stopper containing the mixture of the active compounds a cap may be used made from polyalkylene material especially polyethylene. Such a bottle is described in U.s. Pat. specification No. 2,549,404. In that case it is preferred to dissolve each of the two active compounds separately e.g. in hexane, to mix the solutions in the desired ratio and to fill the cap. Polyethylene is rather permeable to vapours. The solvent rapidly vanishes from the cap and the vapours of the active substances slowly permeate through the wall of the cap. If the cap is placed in a trap, the concentration of the vapours outside the cap and inside the trap is sufficient to attract the males.

It is also possible to impregnate materials with the active mixture such as filter paper, wood, high molecular substances and the like.

We claim:

1. A synergistic composition for attracting the male summerfruit tortrix moth Adoxophyes orana comprising about one part cis-11-tetradecenyl acetate, and about three to nine parts cis-9-tetradecenyl acetate, in combination with a liquid carrier material, said composition containing less than 15% of the corresponding trans compounds.

2. A method for attracting the male summerfruit tortrix moth Adoxophyes orana which comprises subjecting the moth to the biological action of an effective amount of a composition comprising about one part cis-11-tetradecenyl acetate, and about three to nine parts cis-9-tetradecenyl acetate, in combination with a suitable carrier material said composition containing less than 15% of the corresponding trans compounds.

* * * * *

UNITED STATES PATENT AND TRADEMARK OFFICE
CERTIFICATE OF CORRECTION

PATENT NO. : 3,980,771
DATED : September 14, 1976
INVENTOR(S) : Meijer et al

It is certified that error appears in the above-identified patent and that said Letters Patent are hereby corrected as shown below:

Front page, Column 2, change "42109" to --42109s--;
Column 4, line 27, change "such" to --Such--;
Column 4, line 35, change "U.s." to --U.S.--;
Column 4, line 62, before "carrier" insert --liquid--.

Signed and Sealed this

Fifteenth Day of February 1977

[SEAL]

Attest:

RUTH C. MASON
Attesting Officer

C. MARSHALL DANN
Commissioner of Patents and Trademarks